US00PP14212P39

(12) United States Plant Patent
McNeilage et al.

(10) Patent No.: US PP14,212 P3
(45) Date of Patent: Oct. 7, 2003

(54) KIWI PLANT NAMED 'HORTGEM TORU'

(50) Latin Name: *Actinidia deliciosa*
Varietal Denomination: 'Hayward'

(75) Inventors: Mark A McNeilage, Auckland (NZ); Ron A Beatson, Motueka (NZ); Elspeth A MacRae, Auckland (NZ)

(73) Assignee: The Horticulture and Food Research Institute of New Zealand Limited, Palmerston North (NZ)

( * ) Notice: Subject to any disclaimer, the term of this patent is extended or adjusted under 35 U.S.C. 154(b) by 0 days.

(21) Appl. No.: 10/079,142

(22) Filed: Feb. 19, 2002

(65) Prior Publication Data

US 2003/0159187 P1 Aug. 21, 2003

(51) Int. Cl.[7] ..... A01H 5/00

(52) U.S. Cl. ..... Plt./156

(58) Field of Search ..... Plt./156

*Primary Examiner*—Bruce R. Campell
*Assistant Examiner*—June Hwu
(74) *Attorney, Agent, or Firm*—Greenlee, Winner and Sullivan, P.C.

(57) ABSTRACT

A new and distinct kiwi plant of the species *Actinidia arguta* (Sieb. & Zucc.) Planch. ex Miq. var. *arguta* is described. The variety results from a controlled pollination using a female *A. arguta* selection AA01_01 of unknown parentage and a male *A. arguta* selection AA04_01 of unknown parentage. Both named parents (AA01_01 and AA04_01) are unpatented. The new variety is distinguished by its green hairless, edible skin, small fruit size, ovoid shape and sweet aromatic taste.

7 Drawing Sheets

Genus and species of plant claimed: *Actinidia arguta*.
Variety denomination: 'Hortgem Toru'.

BACKGROUND TO THE INVENTION

Kiwi plants in cultivation are mainly varieties of *Actinidia deliciosa*, particularly 'Hayward' although some *A. chinensis* and *A. arguta* varieties are grown. *A. deliciosa* and *A. chinensis* are closely related, whereas *A. arguta* is classified in a separate section of the genus. *A. deliciosa* and *A. chinensis* varieties have large fruit (~100 g ) with hair on the skin. The main varieties in New Zealand are 'Hayward' (*A. deliciosa*) (unpatented) and 'Hort16A' (*A. chinensis*) (U.S. Plant Pat. No. 11,066). Fruit are usually cut and eaten with a spoon. *A. arguta* has small fruit (~10 g) with no hair on the skin. The skin is edible so these fruit can be eaten whole, like a grape.

All Actinidia species are dioecious, so female varieties have to be interplanted with male pollinizers to ensure fruit production.

*A. arguta* vines are deciduous and tend to grow vigorously in spring and summer when rapidly-growing shoots can intertwine and tangle if not managed. Vines do best in a mild temperate climate without late spring or early autumn frosts. They produce consistent heavy crops when grown in well-drained fertile soils and given regular irrigation in dry spells.

*A. arguta* flowers in spring (late October–early December) in New Zealand. Harvest of *A. arguta* fruit may occur between early February and late March in New Zealand depending on the selection and location of plantings. Compared to *A. deliciosa* and *A. chinensis, A. arguta* fruit require more careful handling during harvest and post-harvest procedures.

SUMMARY OF THE INVENTION

The present invention is a new and distinctive kiwi plant having a small, generally ovoid shaped fruit with green hairless edible skin. This new variety is designated 'Hortgem Toru' and is derived from a controlled pollination of AA01_01, a female *A. arguta* selection of unknown parentage (unpatented), with AA04_01, a male *A. arguta* selection of unknown parentage (unpatented).

The female parent was introduced as a plant from Hillier's Nursery, England to New Zealand in 1955. The male parent arose from a seed family collected in the district Aomori, North Honshu, Japan and was introduced to New Zealand in 1977. The provenance of both is unknown.

This new variety was created during the course of a planned plant-breeding program, which was initiated during 1987 at HortResearch in Auckland, New Zealand. The controlled cross was made in November 1987. Seeds were sown in autumn (March) 1988 and 6 seedlings were selected from this cross and were planted out in the field at HortResearch Kumeu Research Orchard in spring (October) 1988. The seedlings first fruited in February–March 1991. Twenty promising female seedlings were clonally propagated into a two-site replicated trial in 1995 and 'Hortgem Toru' (breeding code C3C3) was selected after storage and sensory evaluation in 1998.

The new variety can be asexually reproduced as cuttings or by grafting or budding on to seedling or cutting-grown rootstocks of *A. arguta*. Trial plantings as cuttings established in 1995 at the HortResearch Te Puke and Nelson Research Centres and on seedling rootstocks established in 1998 at these sites have shown that the unique combination of characters come true to form and are established and transmitted through succeeding asexual propagations.

BRIEF DESCRIPTION OF THE ILLUSTRATIONS

Figure 1:
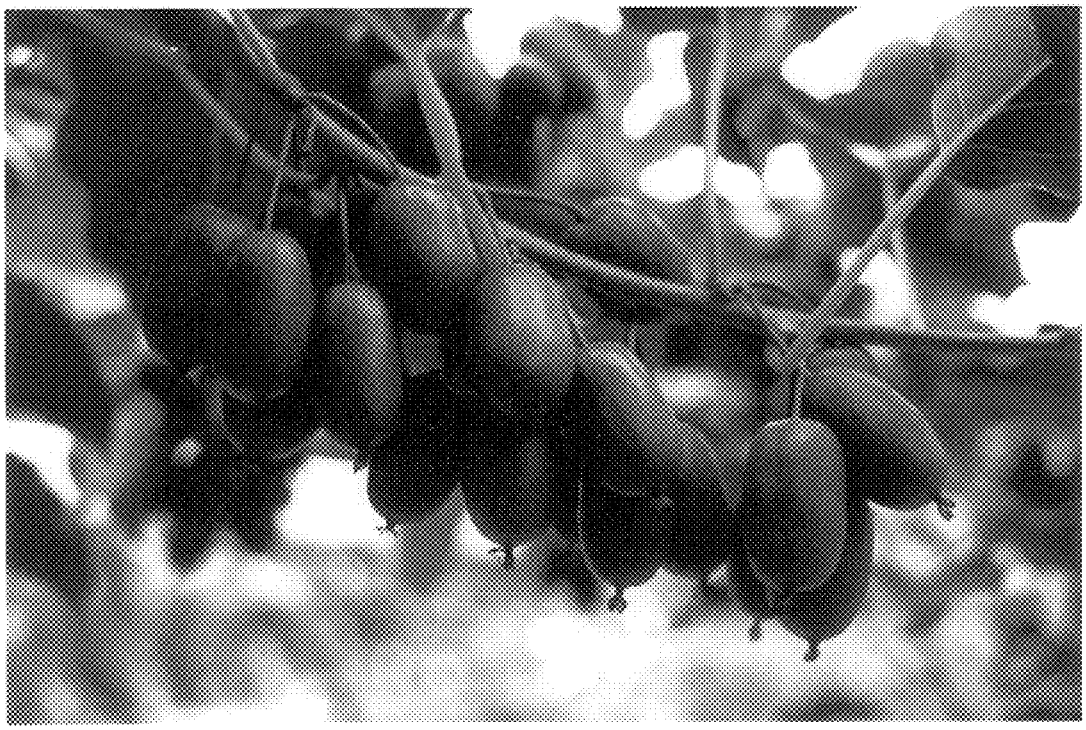
FIG. 1 shows typical fruit of the variety 'Hortgem Toru' in the orchard.
Figure 2:
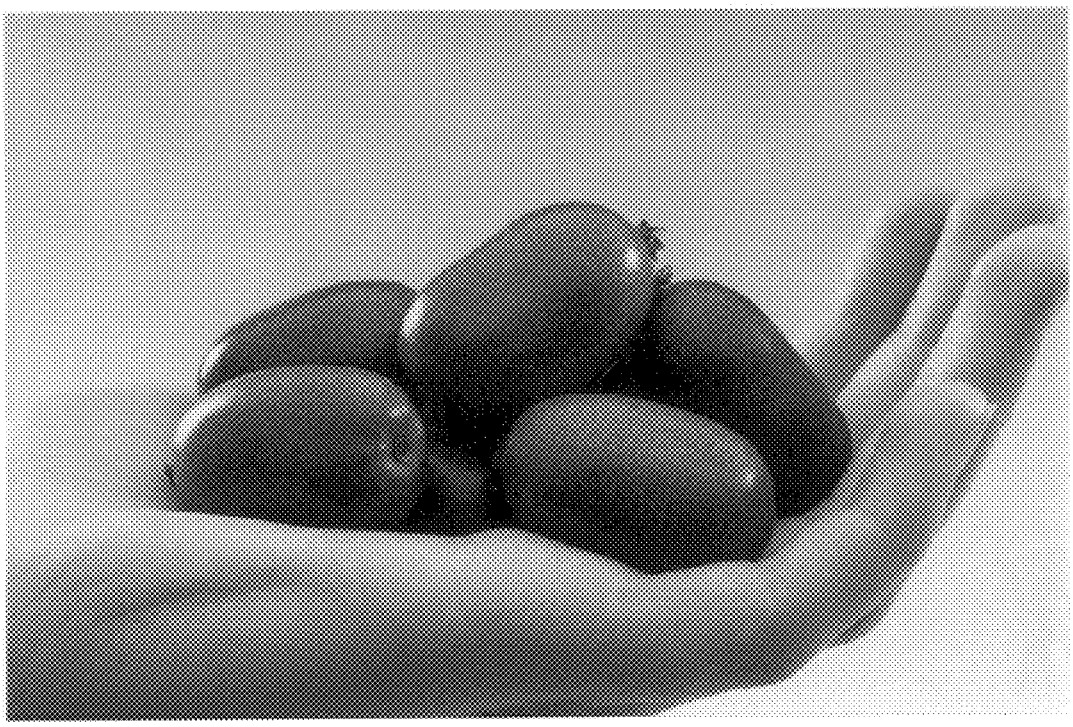
FIG. 2 shows typical fruit of the variety 'Hortgem Toru' in the studio.
Figure 3:
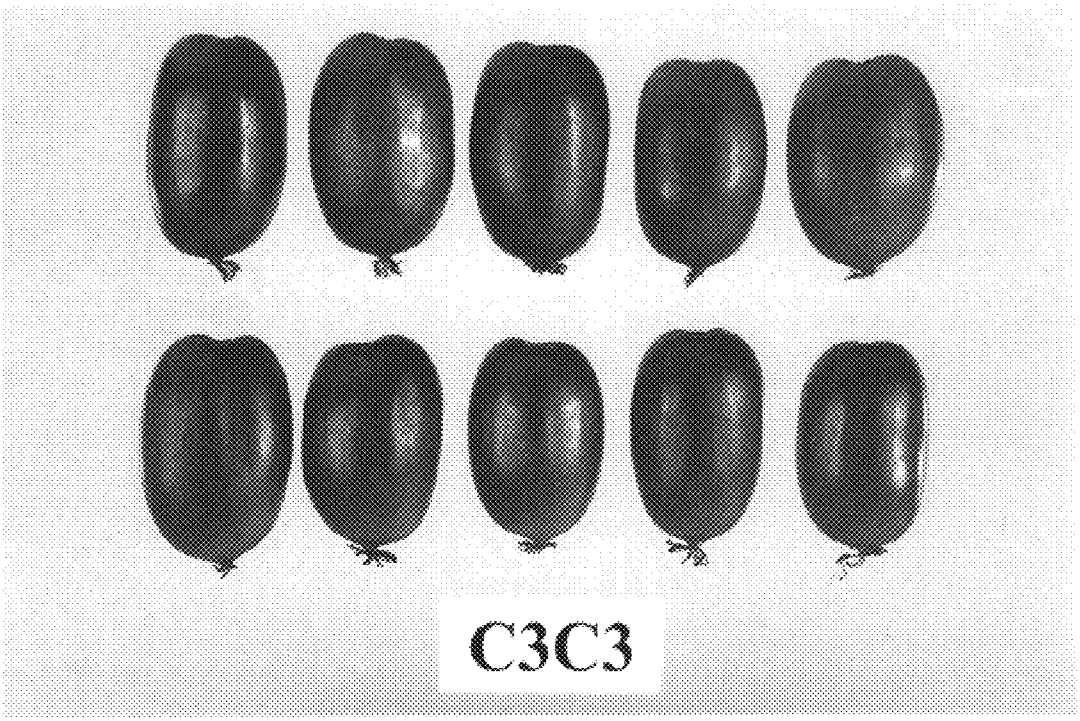
FIG. 3 shows the side view of typical fruit of the variety 'Hortgem Toru'.
Figure 4:
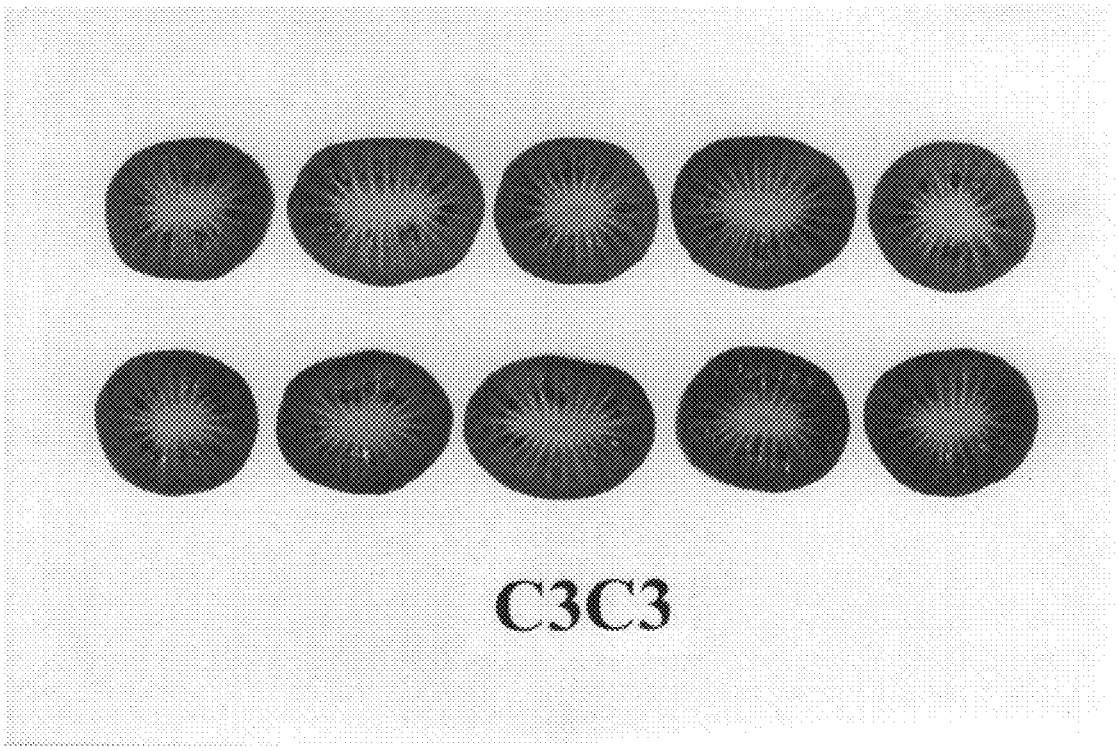
FIG. 4 shows the cross-sectional view of typical fruit of the variety 'Hortgem Toru'.
Figure 5:
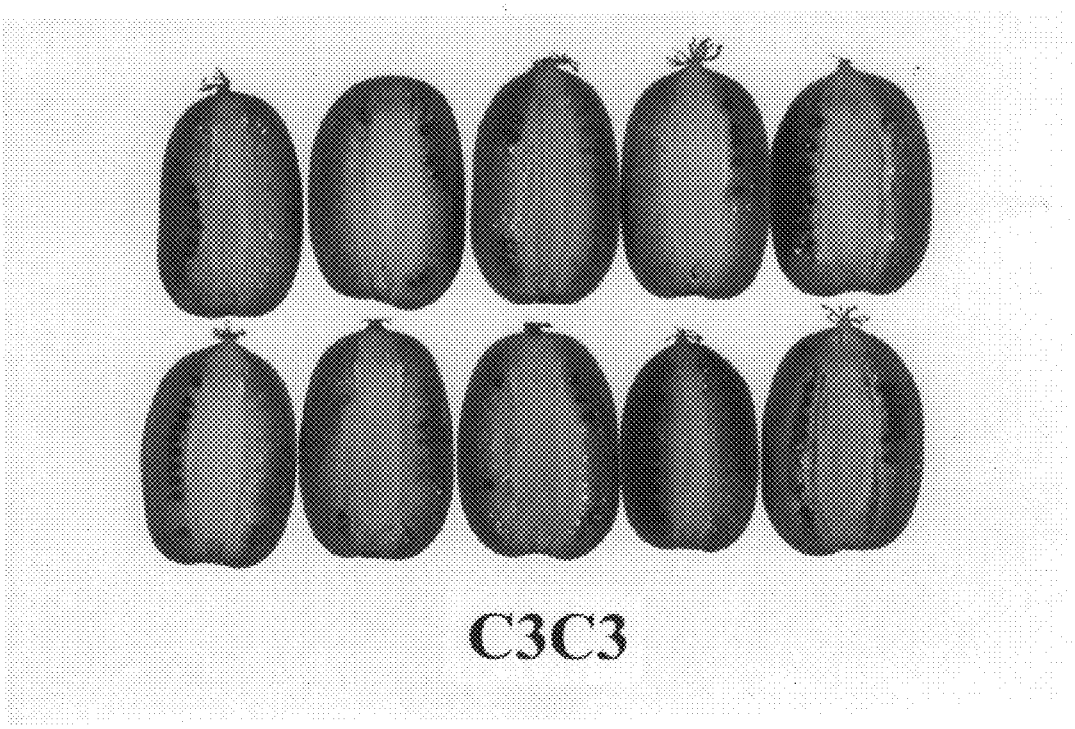
FIG. 5 shows the longitudinal view of typical fruit of the variety 'Hortgem Toru'.
Figure 6:
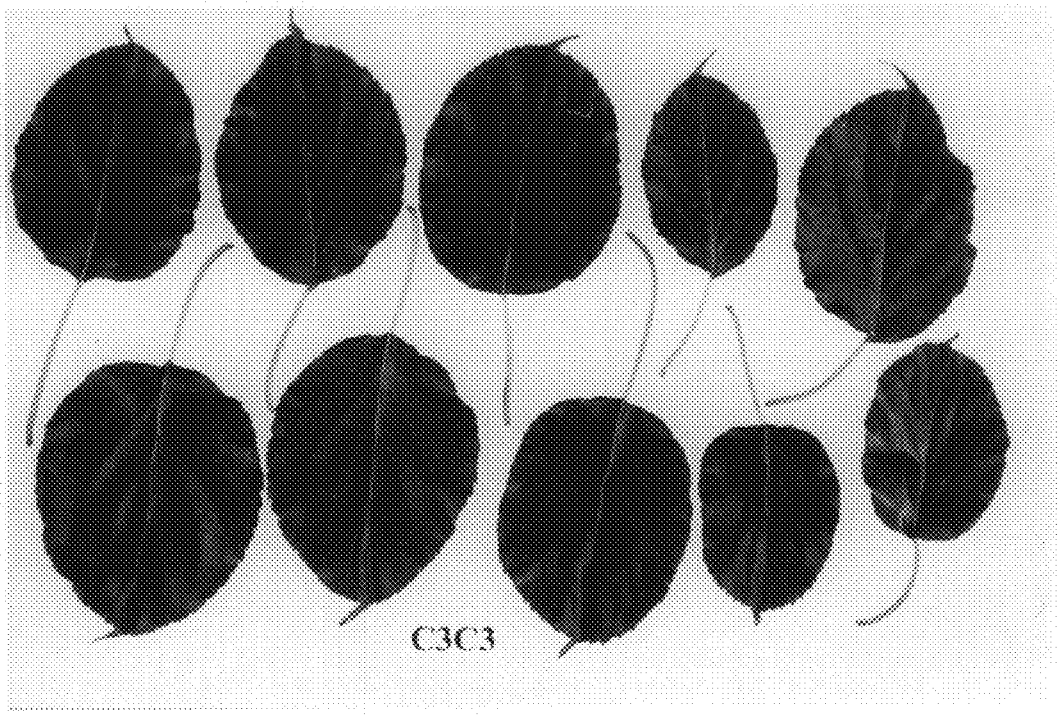
FIG. 6 shows leaves of the variety 'Hortgem Toru'.
Figure 7:
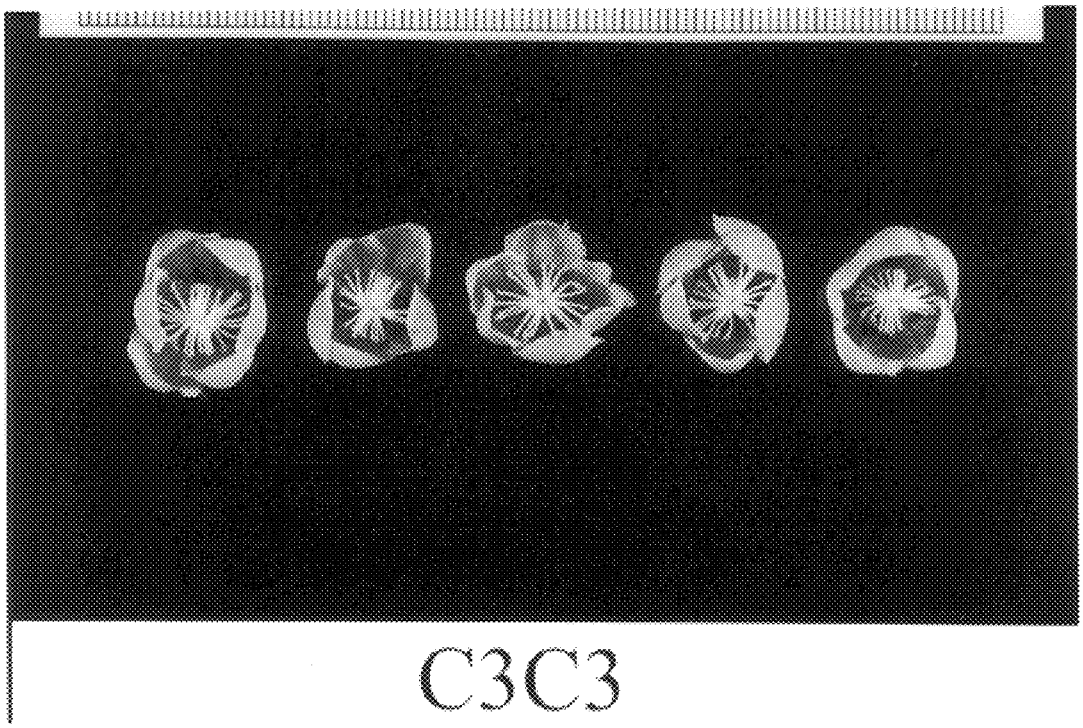
FIG. 7 shows flowers of the variety 'Hortgem Toru'.

Photographs of fruit were taken after the normal harvest date and are depicted in colours as nearly true as is reasonably possible to make the same in a colour illustration of this character. Fruit skin colour may vary depending upon extent of exposure to direct sunlight.

COMPARISON TO CLOSEST VARIETY

The distinctive characteristics of this new kiwi variety, described in detail in Table 1 below, were observed in 2001 at Te Puke, New Zealand. The plants observed were established from cuttings and were 6 years old at the time. 'Hortgem Toru' is a new variety of *A. arguta* distinctive in its own right. Comparison with another similar variety 'Hortgem Tahi' (U.S. Plant Pat. No. 13,815) showed that 'Hortgem Toru' may be distinguished as follows:

Table 1. Comparison with a similar variety.

| Similar variety | Characteristic | Expression of the characteristic for the similar variety | Expression of the characteristic for the candidate variety |
|---|---|---|---|
| *Hortgem Tahi* | Fruit shape | spheroid | ovoid |
| *Hortgem Tahi* | Start of harvest | late Feb | early Feb |
| *Hortgem Tahi* | Storage life of fruit at 0° C. in air storage | 10–12 weeks | 3–4 weeks |

BOTANICAL DESCRIPTION OF THE PLANT

The new variety 'Hortgem Toru' is pistillate, with morphologically perfect but functionally imperfect flowers, i.e. the flowers produce only sterile pollen and thus require a pollinizer for fruit production. Characteristics of the new variety include a short period (~3 months) between flowering and harvest, early harvest, small ovoid fruit with green hairless edible skin, green flesh and a sweet aromatic flavour.

DETAILED DESCRIPTION OF THE VARIETY

Horticultural terminology is used in accordance with revised UPOV guidelines for kiwi. All dimensions in millimeters, weights in grams (unless otherwise stated). Where a colour reference is given these refer to the R.H.S. Colour Chart, The Royal Horticultural Society, London. 3$^{rd}$ Edition, 1995.

Plant and Foliage

This female (flowers imperfect) plant expresses strong vigour. Tomentose hairs are present on the young shoot in medium density. Anthocyanin (red) coloration (near Red 46A) of the growing tip is absent or weakly evident. Otherwise the young shoot is near Green 137D in color. The stem of the plant is thin; averaging approximately 8.4 mm in diameter. The stem color on the exposed side is near Greyed-orange 166B. The bark is smooth and absent of hairs. The lenticels are many (approximately 25–35/cm$^2$), conspicuous, and near Greyed-orange 169D in color. Coloration of the leaf axil is either absent or very weak (near Greyed-orange 176A in color where present) on both the young shoot and the stem. Dormant bud diameter is very small; typically about 0.2 mm in diameter, while the bud support is typically approximately 4.0 mm in diameter. Buds are visible on the dormant cane and dormant buds are absent of hairs. The leaf scar is deep.

The blade of the mature leaf is generally broad ovate, averaging approximately 114.7 mm in length (observed range approximately 97 to 134 mm) and averaging approximately 7.2 mm in width (observed range approximately 67 to 90 mm). The shape of the tip of the blade is caudate while the shape of the base is rounded. The arrangement of the leaf basal lobes is far apart; the distance between lobes averaging approximately 1.94 mm. Puckering or blistering on the upper side of the blade is absent or very weak. The leaf margin is ciliate. The upper side of the blade of the leaf (observed for the mature leaf after petal fall) is near Green 136A. The lower side of the blade of the leaf (observed for the mature leaf after petal fall) is near Green 138A. The upper surface of the leaf exhibits medium glossiness and there is no glaucosity on the lower side of the leaf. The petiole length averages approximately 60.2 mm in length (observed range approximately 46 to 85 mm) and is largely absent of hairs. Anthocyanin (red) coloration on the upper side of the petiole is a similar medium density to the variety Hayward (near Red 54C), otherwise the petiole is near Yellow-green 149C in color.

Infloresence

The predominant number of flowers in the inflorescence is three. The pedicel averages approximately 31.0 mm in length (observed range approximately 28.6 to 33.6 mm) with sparse, very short (averaging approximately 0.4 mm), hairs. There are typically 5 sepals, reddish brown in color (near Red 53B and Grey-brown 199D). The diameter of the terminal or king flower when fully open is small, averaging 23.6 mm (observed range approximately 20.1 to 26.4 mm). The petal length averages approximately 12.4 mm (observed range 11.1 to 13.6 mm) and averages approximately 10.1 mm wide (observed range 8.1 to 12.1 mm). The petal length/width ratio is approximately 1.2 (observed range approximately 1.02 to 1.53). The mean number of petals per flower is approximately 5.4 (observed range approximately 5 to 6). The petals are arranged overlapping and are near green-white 157A in color when fully open. The color is uniform over the entire petal.

The number of stamens averages approximately 39.7 (observed range approximately 38 to 42). The stamen filament averages approximately 3.5 mm in length (observed range approximately 3.0 to 4.1 mm), while the anthers average approximately 2.2 mm in length (observed range 1.5 to 2.8 mm). The filament color is near Green 130D; the anther color varies, near purple black (Black 202A) or near Grey 201B. The number of styles averages approximately 23 (observed range approximately 20 to 29). The styles average 4.8 mm in length (observed range approximately 4.3 to 5.4 mm) and are typically arranged in a horizontal attitude with weak curvature, and are near white in coloration. The length of the ovary averages approximately 7.3 mm (observed range approximately 7.0 to 7.9 mm). The ovary is absent of hairs and is near Yellow-green 145A in color.

Fruit

The fruit are overall small in size, averaging approximately 11.9 g (observed range averaging approximately 9.7 to 13.6 g). The fruit average approximately 34.8 mm in length (observed range approximately 33.0 to 37.0 mm) with a maximum width average approximately 21.6 mm (observed range approximately 20.0 to 23.0 mm) and a minimum width averaging approximately 19.6 mm (observed range approximately 18.0 to 21.0 mm). The locule number averages approximately 20.7 (observed range approximately 18 to 24) with a maximum core diameter averaging approximately 6.7 mm (observed range approximately 5.2 to 9.3 mm) and a minimum core diameter averaging approximately 4.7 mm (observed range approximately 3.9 to 5.4 mm). The peduncle length averages approximately 31.1 mm (observed range approximately 28.3 to 34.0 mm) and the peduncle width averages approximately 1.5 mm (observed range approximately 1.3 to 2.0 mm). The general shape of the fruit is oblong although the cross-section at the median of the fruit is oblate in shape. The stylar end of the fruit is typically slightly pointed, protruding, and the shape of the shoulder on the stalk end is typically rounded. The fruit skin color at harvest (fruit still hard) is medium green (within the range of near Green 137C and near Green 141B). There is little skin color change during ripening and the skin color at maturity for consumption is medium green (within the range of near Green 137A and near Green 139B). The fruit skin is absent of hairs.

The fruit core is medium in diameter (averaging approximately 6.72 mm at the largest diameter), is oblate in cross-section, and is near green white in color (within the range of near Yellow-green 150D and near Green-white 157B) at harvest. There is no woody spike. The color of both the outer pericarp, and the inner pericarp (locules), at maturity for consumption are green (within the range of near Green 137A and near Green 141B). Seed is small (maximum average diameter approximately 1.33 mm; maximum average length approximately 2.01 mm). The seed color at maturity, in the flesh at fruit maturity is dark brown (near Brown 200B) and brownish-orange when dry (within the range near Greyed-orange 172B and near Greyed-orange 175C).

Cultivation

Vegetative budbreak occurs late August, early September in New Zealand, whilst flowering commences about late October, early November. The time of fruit maturity for harvest at nominated Brix level) occurs approximately early February.

No pest and disease resistance has been observed. The plant hardiness range (according to the American zone classification) has not been determined. Under New Zealand conditions, the plants are grown in areas that experience some winter cold and frost, estimated to be equivalent to the minimum temperature ranges of zones 8 and 9.

HORTICULTURAL CHARACTERISTICS

Details below relate to observations made on cutting-grown plants growing at HortResearch Te Puke Research Centre, New Zealand. These vines were 3 years old.

Cropping: Young vines of 'Hortgem Toru' are precocious, beginning to bear in their second year and are expected to reach full capacity at about 7 years. The storage life of 'Hortgem Toru' fruit is 3–4 weeks at 0° C., if stored in unventilated containers in air storage.

Yield and fruit size: (Data from harvesting all fruit from 6 vines in early February 1999).

Mean fruit weight: 11.85 g Maximum: 13.57 g Minimum: 9.66 g.

Mean fruit number: 356 Maximum: 922 Minimum: 2.

Mean yield: 4.2 kg Maximum: 10.7 kg Minimum: 0.027 kg.

It is anticipated mature, well-managed vines would yield approximately 5000 fruit per vine with a mean fruit weight of 10 g and mean yield per vine of 50 kg.

We claim:

1. A new and distinct kiwi plant of the species *A. arguta* substantially as described and illustrated, characterised by small ovoid fruit with green hairless edible skin and green flesh with a sweet aromatic flavour.

* * * * *

C3C3